(12) United States Patent
Schmid

(10) Patent No.: US 7,659,108 B2
(45) Date of Patent: Feb. 9, 2010

(54) FERMENTER COMPRISING AN AGITATOR

(75) Inventor: Walter Schmid, Glattbrugg (CH)

(73) Assignee: Kompogas AG (CH)

( * ) Notice: Subject to any disclaimer, the term of this patent is extended or adjusted under 35 U.S.C. 154(b) by 376 days.

(21) Appl. No.: 11/814,634

(22) PCT Filed: Nov. 4, 2005

(86) PCT No.: PCT/CH2005/000646

§ 371 (c)(1),
(2), (4) Date: Jul. 24, 2007

(87) PCT Pub. No.: WO2006/079227

PCT Pub. Date: Aug. 3, 2006

(65) Prior Publication Data

US 2008/0138888 A1    Jun. 12, 2008

(30) Foreign Application Priority Data

Jan. 26, 2005    (CH) ........................ 122/05

(51) Int. Cl.
*C12M 1/00* (2006.01)
*C12M 3/00* (2006.01)

(52) U.S. Cl. .................. 435/293.1; 435/289.1

(58) Field of Classification Search .......... 435/170, 435/289.1–293.1, 298.1, 296.1; 366/325.1–325.3
See application file for complete search history.

(56) References Cited

U.S. PATENT DOCUMENTS

| 2,306,960 | A |   | 12/1942 | Kinnucan |         |
|-----------|---|---|---------|----------|---------|
| 2,793,166 | A | * | 5/1957  | Hatch    | 435/289.1 |
| 3,028,314 | A | * | 4/1962  | Means et al. | 435/43 |
| 3,367,126 | A |   | 2/1968  | Howell   |         |
| 4,514,297 | A |   | 4/1985  | Enqvist  |         |
| 5,431,860 | A | * | 7/1995  | Kozma et al. | 261/93 |
| 5,939,313 | A | * | 8/1999  | Cheng    | 435/289.1 |
| 2004/0043480 | A1 | * | 3/2004 | Bouldin | 435/290.2 |
| 2008/0032375 | A1 | * | 2/2008 | Hartmann et al. | 435/170 |

FOREIGN PATENT DOCUMENTS

| DE | 3149344 A1 | 9/1983 |
| DE | 19648875 A1 | 5/1998 |
| EP | 0324894 A2 | 7/1989 |
| EP | 0476217 A1 | 3/1992 |
| EP | 0621336 A2 | 10/1994 |
| EP | 0770675 A1 | 5/1997 |
| EP | 1332805 A1 | 8/2003 |

* cited by examiner

*Primary Examiner*—Jill Warden
*Assistant Examiner*—Shanta G Doe
(74) *Attorney, Agent, or Firm*—Ziolkowaski Patent Solutions Group, SC

(57) ABSTRACT

A plug-flow operated, horizontal fermenter for anaerobic fermentation of biogenic waste includes a fermenter tank having an inlet and an outlet that is configured to be filled with a biomass material. The fermenter also includes an agitator having a shaft passing through the fermenter tank in its longitudinal direction, wherein the shaft is mounted in end regions of the fermenter tank and is designed as a closed, hollow shaft having an inner space filled with gas or air. A plurality of agitator arms are arranged on the shaft. The inner space of the shaft is monitored with respect to a gas or air pressure to ensure that a buoyancy of the shaft in the filled fermenter tank at least approximately compensates for a sagging of the shaft.

13 Claims, 2 Drawing Sheets

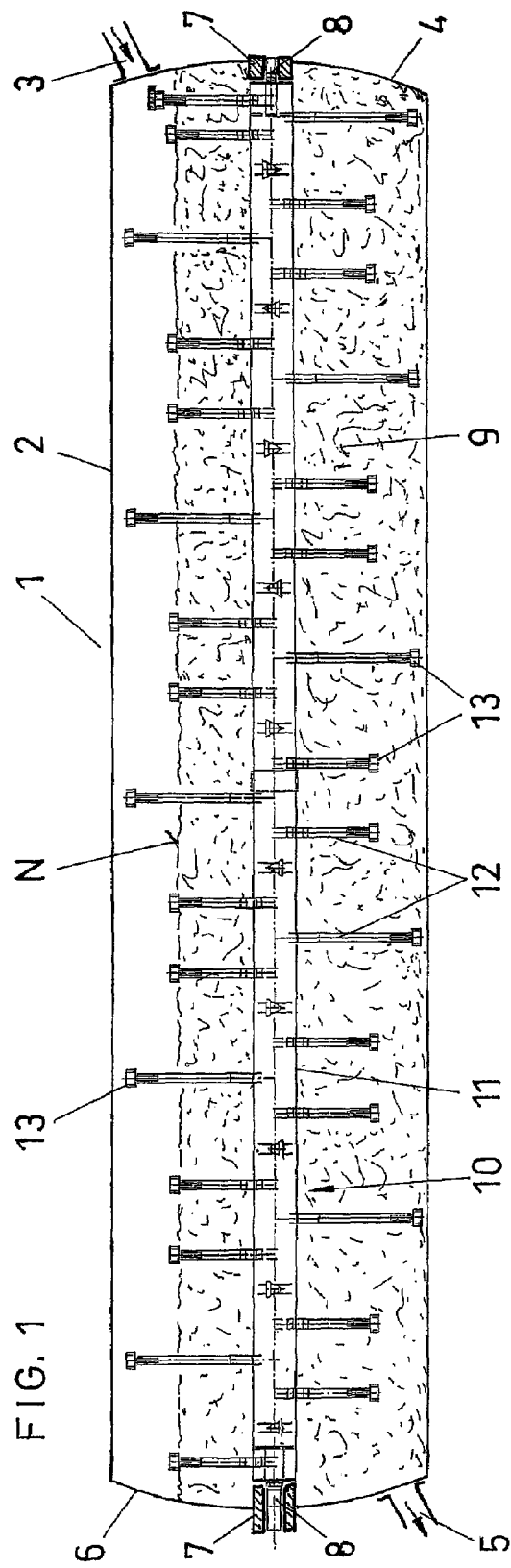
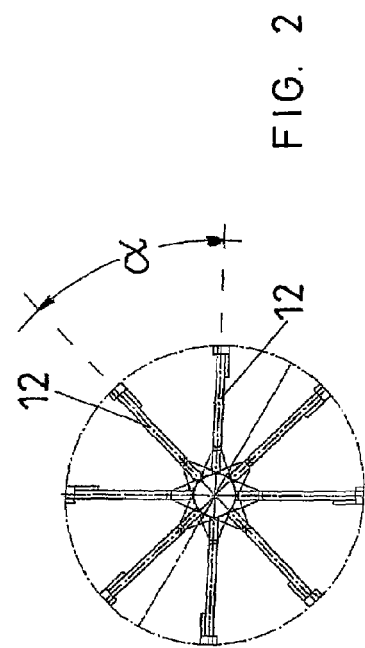

FERMENTER COMPRISING AN AGITATOR

BACKGROUND OF THE INVENTION

The present invention relates to a plug-flow operated fermenter for anaerobic fermentation of biogenic waste, with an inlet and an outlet, and with an agitator which consists of a shaft passing through the fermenter in its longitudinal direction, on which a multitude of agitator arms are arranged, wherein the shaft is mounted in the region of the fermenter ends.

The applicant is the worldwide leader in providing installations for producing biogas from biogenic waste. The basic construction of such installations is to be deduced from the European patent document EP-0'476'217-A. The installations operate according to a method according to the European Patent EP-B-621'336. The firstly mentioned patent document discloses a plug-flow operated, horizontal fermenter which is suitable for the anaerobic fermentation of biogenic waste. The fermenter is an elongated, horizontal tank with an inlet provided at one end, and with an outlet present at the oppositely lying end. The biogenic waste, reduced in size, is fed in at the inlet side and is inoculated with fermented material and/or press water from the processing. The material to be fermented is enriched with methane bacteria by way of this. The biogenic waste, amid controlled thorough mixing, is decomposed while forming biogas, and subsequently led through the outlet for aerobic decay after the exit.

The worldwide demand for installations of systems of the type mentioned above to have increasing capacities also leads to ever-larger fermenters being built. In order to render this possible, the fermenter tanks must be set up on location, wherein this may be effected either by way of a segmented joining-together into a steel tank, or, as is known from EP-770'675-A, the horizontal fermenter tank may be set up on location from concrete. Nowadays, horizontal fermenter tanks are realized with a total length of over 50 meters and a diameter of over 10 meters for increasing the capacity. In previous systems, the shaft of the agitator was designed as a solid steel shaft. This is possible without any problems with lengths below 20 meters. If greater lengths are required, then the intrinsic weight of the shafts leads to a sagging, which is a problem. The agitator indeed must not only thoroughly mix the biogenic waste in order to achieve a certain homogeneity, but one must simultaneously also ensure that heavy solid matter, in particular such as sand and stones, do not sediment at the bottom of the fermenter tank and as a result may no longer be carried away. Although the fermenter is operated in plug-flow, the through-flow is not capable of carrying away the sinking heavy substances, since the plug-flow movement only has a low flow speed. The throughput time of the biogenic waste through the fermenter from the inlet to the outlet, in fact, is several days. The agitator as a result of this, apart from thoroughly mixing, likewise contributes to conveying this heavy matter upwards from the base again, in order afterwards to be transported with the subsequent sinking movement in the plug-flow, in the direction of the fermenter outlet. Accordingly, the agitator consists of a shaft passing through the fermenter, with a multitude of agitator arms, which at their end distant to the shaft are provided with suitable blades.

With greatly dimensioned fermenters, the sagging of the shaft has led to the blades practically brushing along on the fermenter wall, and accordingly the occurrence of defects of the fermenter after a few years of operation. In the most obvious solution, the shaft is mounted by way of intermediate supports. This solution however has not proven itself suitable, since the supports upset the plug-flow operation.

Finally, a fermenter is known from DE-A-31'49'344, which comprises an agitator which is provided with tank-like agitator arms. These agitator arms are designed such that gas may be pumped into these amid the displacement of fluid components from these tank-like agitator arms, so that their buoyancy effects a rotational movement of the agitator, without a driven shaft being required.

It is therefore the object of the invention to provide a solution which avoids a sagging of the shaft, and rules out damage resulting from this.

BRIEF DESCRIPTION OF THE INVENTION

The present invention solves the aforementioned problem by providing a plug-flow operated, horizontal fermenter.

According to one aspect of the invention, a plug-flow operated, horizontal fermenter for anaerobic fermentation of biogenic waste includes a fermenter tank having an inlet and an outlet that is configured to be filled with a biomass material. The fermenter also includes an agitator having a shaft passing through the fermenter tank in its longitudinal direction, wherein the shaft is mounted in end regions of the fermenter tank and is designed as a closed, hollow shaft having an inner space filled with gas or air. A plurality of agitator arms are arranged on the shaft. The inner space of the shaft is monitored with respect to a gas or air pressure to ensure that a buoyancy of the shaft in the filled fermenter tank at least approximately compensates for a sagging of the shaft.

Further advantageous designs of the subject-matter of the invention are to be deduced from the dependent claims. Their design, purpose and effect are explained in the subsequent description with reference to the accompanying drawings.

BRIEF DESCRIPTION OF THE DRAWINGS

The drawings illustrate one preferred embodiment presently contemplated for carrying out the invention.

In the drawings:

FIG. 1 is a vertical longitudinal section through a fermenter according to the invention.

FIG. 2 is a vertical section through the fermenter transverse to the longitudinal direction of the shaft.

DETAILED DESCRIPTION OF THE PREFERRED EMBODIMENT

Figure 4:
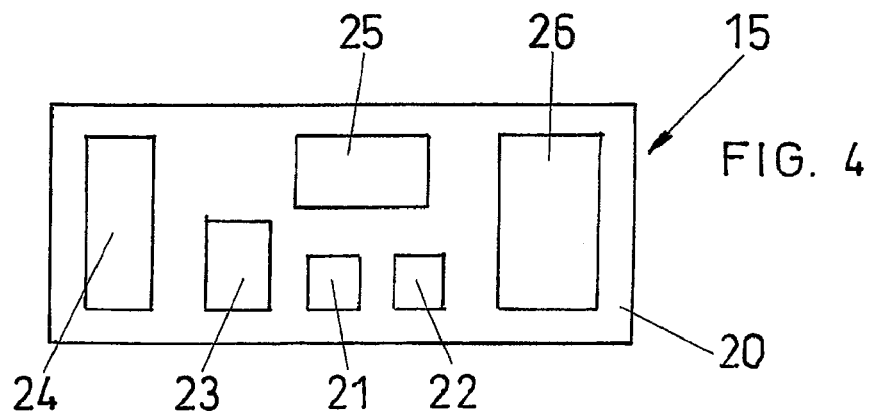
FIG. 4 is a wireless sensor monitoring unit in a schematic representation.

The horizontal fermenter according to the invention is shown in its entirety in a vertical longitudinal section in FIG. 1. The complete fermenter is indicated at 1. This comprises the fermenter tank 2 which may be manufactured of steel or concrete. An inlet 3 is present at the one side in the end-wall 4 on the inlet side. An outlet 5 is present on the oppositely lying side in the end-wall 6 on the outlet side. In each case, a shaft bearing 7 is integrally formed in the two end-walls 4 and 6, in which the shaft 10 is mounted with its terminal shaft journals 8.

The shaft 10 comprises the two shaft journals 8 which are connected to a shaft body 11 in a rotationally fixed manner.

The shaft body 11 consists of steel tube which is hermetically sealed at both sides. A multitude of agitator arms 12 are attached on the shaft body 11 by way of a suitable welding design. Each agitator arm 12 comprises terminal blades 13.

A preferred solution lies in the tube forming the shaft body 11 being provided with shaft journals 8 integrally formed at one or both sides. Here, the drive is effected at one or both sides via one or both shaft journals. One variant lies in leading the tube forming the shaft body 11 through the end-walls 4, 6 of the fermenter at one side or both sides, and realizing the drive at one or both sides for example by way of a crown gear attached on the tube.

Figure 3:
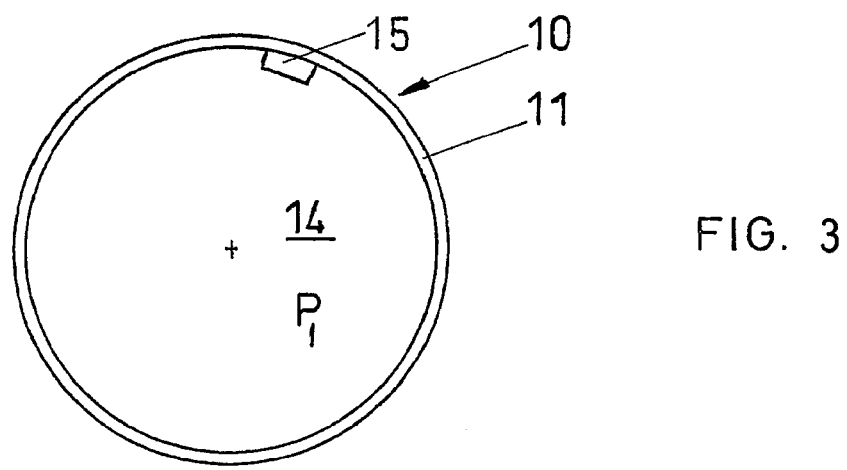
FIG. 3 shows a schematic cross section through the hollow shaft in the region of a sensor.

As a result, the shaft 10 is designed as a hollow shaft. In the sectioned drawing according to FIG. 3, one may recognize the shaft body 11 and its inner space 14. According to the embodiment represented here, a sensor monitoring unit 15 is attached on the inner wall of the shaft body 11 formed out of a tube. A predefined, applied pressure prevails in the inner space 14 of the shaft body 11. This pressure is indicated at $P_1$. The pressure $P_1$ in the inner space 14 may be an overpressure or an underpressure. The monitoring of the inner pressure $P_1$ by way of the sensor monitoring unit 15 may be effected in a conventional manner via suitable electrical leads which are led to the outside in the region of the shaft journal, or, as shown here and explained later with reference to FIG. 4, by way of wireless communication.

Figure 5:
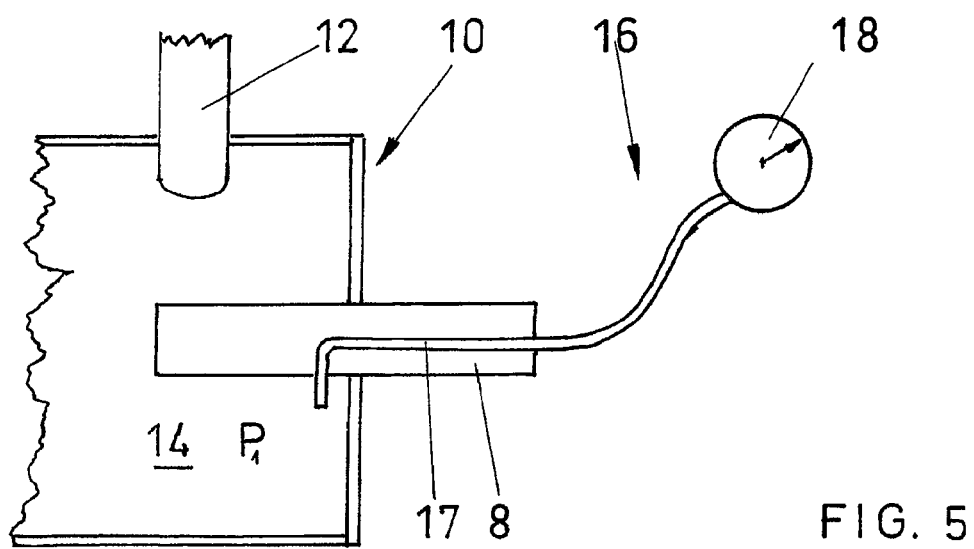
FIG. 5 shows a conventional pressure monitoring through the shaft journals of the hollow shaft according to the invention.

As is shown in FIG. 5, the monitoring of the inner pressure $P_1$ may also be effected in a conventional manner, by way of providing a pressure monitoring unit 16 which consists of a pressure conduit 17 and a manometer 18 connected thereto. Basically, the pressure $P_1$ in the inner space 12 may be selected as an overpressure or as an underpressure. Inasmuch as this is concerned, this is of no significance, since in principle any form of pressure change in the inner space 14 is an indication of a leakage, which must lead to a stoppage of the installation and in particular to a stoppage of the agitator.

The present invention, in principle, is based on the concept of the hollow shaft in the operating condition being continuously and completely immersed in the biomass to be fermented. By way of this, the shaft, thanks to its design as a hollow shaft, displaces a relatively large volume and accordingly the inner space 14 in the shaft 10 effects a buoyancy which at least partly compensates the weight of the shaft 10 or the shaft body 11 with the agitator arms 12 fastened thereto, with the blades 13. Since however, after a multiyear operational duration, the probability of possible leakage increases due to tension fractures or mechanical defects, and in particular also corrosion damage, which leads to these leakages, sooner or later humidity penetrates into the hollow shaft which would change the total weight of the shaft 10 and would accordingly lead to the damage mentioned earlier. Since an optical control may neither be realized in a technically reasonable manner, nor may the respective damage, to some extent the size of a hairline crack, be recognized, the invention proceeds from a manometric monitoring of the inner space 14. Each effect of the shaft which leads to a leakage, automatically leads to a pressure change being effected in the inner space 14. The predefined pressure $P_1$ changes as a result of this. If the inner pressure $P_1$ is applied as an underpressure, then the pressure would increase, and if the inner pressure $P_1$ is applied as an overpressure, then this inner pressure would drop. In any case however, the pressure change is a secure indicator that a leakage is present. The extent of the pressure change may furthermore provide a hint as to the size of the damage. In the normal case, such a pressure change would lead to the installation being run down, i.e. the supply of the biogenic waste is terminated, and the fermenter continues to be operated at operating conditions and successively emptied. A large overpressure may be applied in the inner space 14 for searching for the leakage, in order thus to be able to determine the outflow of air, and thus to be able to localize the location of damage. It is however assumed that such events of damage are relatively seldom cases.

Since the degree of filling of the fermenter 1 is mostly effected up to a level N which lies far above the middle of the fermenter, the shaft 10 to all intents and purposes is always practically completely within the region of the biogenic mass (i.e., the shaft is immersed in the biogenic mass), so that the buoyancy is always present. It would be desirable if the buoyancy of the shaft 10 in the middle region were to be larger with respect to the longitudinal direction, than at the ends. The support function at the ends is taken up, in any case, largely by the respective shaft bearings 7 in which the shaft journals 8 are mounted. In order to realize this possibility, it is envisioned to manufacture the agitator arms 12 in the central region of the shaft 10 from closed tubes. It is further envisioned for these tubes of the agitator arms 12 to likewise communicate with the inner space 14 of the shaft 10.

In any case, it is necessary for the agitator arms to be arranged in a regularly distributed manner with respect to the periphery of the shaft. However, it is not absolutely necessary for a uniform distribution of the agitator arms 12 over the length of the shaft. It is therefore indeed possible and meaningful to increase the density of the agitator arms in the region on the inlet side and outlet side. The sedimentation of solid matter in particular in these relatively sensitive regions is reduced by way of this. The relative freedom of the arrangement of the agitator arms and their design leads to the fact that the buoyancy of the shaft may as a whole be largely balanced.

The distribution of the agitator arms on the periphery of the shaft 10 should be uniform. Most preferably, the relative angle $\alpha$ between two agitator arms 12 adjacent one another in the longitudinal direction is between 90° and 30° and in particular the angle is preferably $\alpha$ 45°.

The finished component 20 represented schematically in FIG. 4 is a sensor monitoring unit 15, as is for example known from vehicle technology for the wireless monitoring of the tire pressure, in particular with lorries. For this, the document US-2004/0155764-A may be referred to.

Such a finished component 20 consists of a base plate on which a pressure sensor 21 is attached. Additionally, but not necessarily, a further sensor 22 may be provided which is designed as a temperature sensor or a hygroscope sensor. A temperature sensor serves essentially for realizing certain pressure fluctuations caused by temperature, so that these do not lead to erroneous interpretation.

A transmission antenna 24 may receive high-frequency signals which may be converted into direct current, and form a feed unit 26. This energy then feeds a microcomputer 25 which evaluates the data of the sensors 21, 22 and delivers a signal to a radio transmitter 23. The sent signal is evaluated by a monitoring of the complete fermentation installation, and as the case may be, may lead to the agitator being switched off and/or the installation being run down.

A hygroscopically acting sensor may for example serve to ascertain an increase in the humidity in the inner space 14 of the shaft 10, which may be an indicator for indicating that condensation water is present in the shaft. The presence of condensation water may also be seen as an indication that a minimal leakage is present. In any case, the formation of condensation water in the shaft is not desired, since damage due to correction would tend to take place. With the dimensions of the fermenter provided here, with a total length between usually 25-50 m length and a diameter between 5 and 15 m, accordingly also the shaft 10 has a shaft body 11 with a diameter which may be between 500 and 1500 mm.

With these dimensions, it is of course possible without any problem, to provide the shaft with an entrance port. Suitable overhaul work may be carried out by way of this entrance port. The entrance port must of course be able to be closed in an absolutely tight manner. The presence of an entrance port is however not essential. With any possible damage, this may also be dealt with by way of overhaul work from the outside. Problems with regard to stiffening in this region are avoided by way of omitting an entrance port, just as additional leakage sources.

The principle of the invention, as already mentioned, lies essentially in designing the shaft 10 as a hollow shaft, and this having a suitable buoyancy. Thereby, one must ensure that one is in the position of monitoring whether the hollow shaft fills with water via a leak. In this case, the buoyancy would cease to exist and the shaft would, accordingly, sag more and more, whereupon unavoidable, respective damage would occur. In order to exclude this possibility, according to the invention, a predefined overpressure or underpressure is applied in the inner space 14 of the shaft, and this pressure is monitored by way of suitable means.

Therefore, according to one embodiment of the invention, a plug-flow operated, horizontal fermenter for anaerobic fermentation of biogenic waste includes a fermenter tank having an inlet and an outlet that is configured to be filled with a biomass material. The fermenter also includes an agitator having a shaft passing through the fermenter tank in its longitudinal direction, wherein the shaft is mounted in end regions of the fermenter tank and is designed as a closed, hollow shaft having an inner space filled with gas or air. A plurality of agitator arms are arranged on the shaft. The inner space of the shaft is monitored with respect to a gas or air pressure to ensure that a buoyancy of the shaft in the filled fermenter tank at least approximately compensates for a sagging of the shaft.

The present invention has been described in terms of the preferred embodiment, and it is recognized that equivalents, alternatives, and modifications, aside from those expressly stated, are possible and within the scope of the appending claims.

What is claimed is:

1. A plug-flow operated, horizontal fermenter for anaerobic fermentation of biogenic waste comprising:
   a fermenter tank having an inlet and an outlet, the fermenter tank configured to be filled with a biomass material;
   an agitator including a shaft passing through the fermenter tank in its longitudinal direction, wherein the shaft is mounted in end regions of the fermenter tank and is designed as a closed, hollow shaft having an inner space filled with gas or air;
   a plurality of agitator arms arranged on the shaft; and
   wherein the inner space of the shaft is monitored with respect to a gas or air pressure to ensure that a buoyancy of the shaft in the filled fermenter tank at least approximately compensates for a sagging of the shaft.

2. The plug-flow operated fermenter according to claim 1 wherein the gas or air pressure in the inner space is a monitored over-pressure ($P_1$).

3. The plug-flow operated fermenter according to claim 1 wherein the gas or air pressure in the inner space is a monitored under-pressure ($P_1$).

4. The plug-flow operated fermenter according to claim 1 further comprising a member arranged in the inner space configured to measure the pressure and output a monitored measured value.

5. The plug-flow operated fermenter according to claim 1 wherein the agitator arms are arranged at regular distances along the shaft and offset along a periphery of the shaft at a same angle over an entire length of the shaft.

6. The plug-flow operated fermenter according to claim 5 wherein two agitator arms adjacent one another in a longitudinal direction of the shaft are arranged to be offset by an angle ($\alpha$) between 30° and 90°, and preferably by 45°.

7. The plug-flow operated fermenter according to claim 1 wherein the shaft further comprises a pair of shaft journals, the shaft journals passing through the end regions of the fermenter tank on the inlet and outlet sides and being mounted outside the fermenter tank.

8. The plug-flow operated fermenter according to claim 7 wherein the shaft further comprises a drive side end connected to one of the shaft journals, the shaft being driven at least at the drive side end by one of the shaft journals.

9. The plug-flow operated fermenter according to claim 8 wherein the shaft, at least at the drive side end, is led through one of the end regions of the fermenter tank and is driven via a crown gear attached thereon.

10. The plug-flow operated fermenter according to claim 7 further comprising a pressure conduit leading into the inner space of the shaft, the pressure conduit being guided through one of the pair of shaft journals to a measurement apparatus.

11. The plug-flow operated fermenter according to claim 1 further comprising a sensor monitoring unit having at least one measurement probe therein, the measurement probe positioned in the inner space of the shaft, and wherein the sensor monitoring unit may be excited from outside the fermenter tank to deliver a signal corresponding to measured data via a transmitter to a receiver arranged outside the fermenter tank.

12. The plug-flow operated fermenter according to claim 1 wherein a change of the air or gas pressure measured in the inner space of the shaft causes a signal to be delivered to a control installation of the fermenter.

13. The plug-flow operated fermenter according to claim 1 wherein in at least one of the agitator arms is formed as a hollow element to increase the buoyancy of the shaft.

* * * * *